United States Patent
Hashimoto et al.

(10) Patent No.: US 7,510,530 B2
(45) Date of Patent: Mar. 31, 2009

(54) PULSE WAVE MEASURING APPARATUS

(75) Inventors: Masao Hashimoto, Kyoto (JP);
Kazuhisa Tanabe, Kyoto (JP); Hironori Satoh, Kyoto (JP); Takashi Inagaki, Kyoto (JP); Ryo Fukui, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 561 days.

(21) Appl. No.: 10/947,240

(22) Filed: Sep. 23, 2004

(65) Prior Publication Data
US 2005/0070806 A1 Mar. 31, 2005

(30) Foreign Application Priority Data
Sep. 25, 2003 (JP) ............................ 2003-333617

(51) Int. Cl.
*A61B 5/02* (2006.01)
(52) U.S. Cl. .................. 600/490; 600/485; 600/498; 600/499; 600/500
(58) Field of Classification Search ................. 600/490, 600/492, 498, 500, 503, 301, 344, 483, 485, 600/491, 493–497, 499, 513
See application file for complete search history.

(56) References Cited

U.S. PATENT DOCUMENTS

| | | | |
|---|---|---|---|
| 3,527,204 A * | 9/1970 | Steinbeck et al. | 600/496 |
| 4,206,754 A * | 6/1980 | Cox et al. | 128/204.21 |
| 4,262,674 A * | 4/1981 | Uemura et al. | 600/493 |
| 4,285,340 A * | 8/1981 | Gezari et al. | 128/205.24 |
| 4,549,550 A * | 10/1985 | Kami | 600/499 |
| 4,566,463 A * | 1/1986 | Taniguchi et al. | 600/495 |
| 4,627,440 A * | 12/1986 | Ramsey et al. | 600/495 |
| 4,780,824 A * | 10/1988 | Niwa et al. | 600/513 |
| 4,790,325 A * | 12/1988 | Lee | 600/490 |
| 4,800,892 A * | 1/1989 | Perry et al. | 600/490 |
| 4,995,399 A * | 2/1991 | Hayashi et al. | 600/493 |

(Continued)

FOREIGN PATENT DOCUMENTS

EP 0356016 A1 2/1990

(Continued)

OTHER PUBLICATIONS

Notice of Grounds of Rejection, mailed Jul. 1, 2008, directed to counterpart Japanese Patent Application No. 2003-333617. 4 pages.

*Primary Examiner*—Patricia C Mallari
(74) *Attorney, Agent, or Firm*—Morrison & Foerster LLP

(57) ABSTRACT

A pressing cuff presses a pressure sensor above an artery. The level of the pressure applied to the pressure sensor is changed while the pulse wave is measured based on information about the pressure from the pressure sensor. In order to adjust the level of the applied pressure using the pressure of gas in the pressing cuff, a three-port valve and a two-port valve are controlled so that the connection is changed to establish a state of holding the amount of the gas in the pressing cuff. Then, the state is changed to a state of isolating and discharging gas in which a part of the held gas is isolated from the remaining amount of the gas to be discharged. Then, the state is changed to the state of holding the remaining amount of gas in the pressing cuff.

5 Claims, 9 Drawing Sheets

U.S. PATENT DOCUMENTS

| | | | | |
|---|---|---|---|---|
| 5,094,244 | A | * 3/1992 | Callahan et al. | 600/490 |
| 5,099,851 | A | * 3/1992 | Hata et al. | 600/485 |
| 5,107,848 | A | * 4/1992 | Oku | 600/499 |
| 5,119,824 | A | * 6/1992 | Niwa | 600/500 |
| 5,447,163 | A | 9/1995 | Apple | |
| 6,164,933 | A | 12/2000 | Tani et al. | |

FOREIGN PATENT DOCUMENTS

| | | |
|---|---|---|
| EP | 0671144 A1 | 9/1995 |
| EP | 0818176 A1 | 1/1998 |
| EP | 1230897 A1 | 8/2002 |
| JP | 60-81504 | 6/1985 |
| JP | 63-293424 | 11/1988 |

* cited by examiner

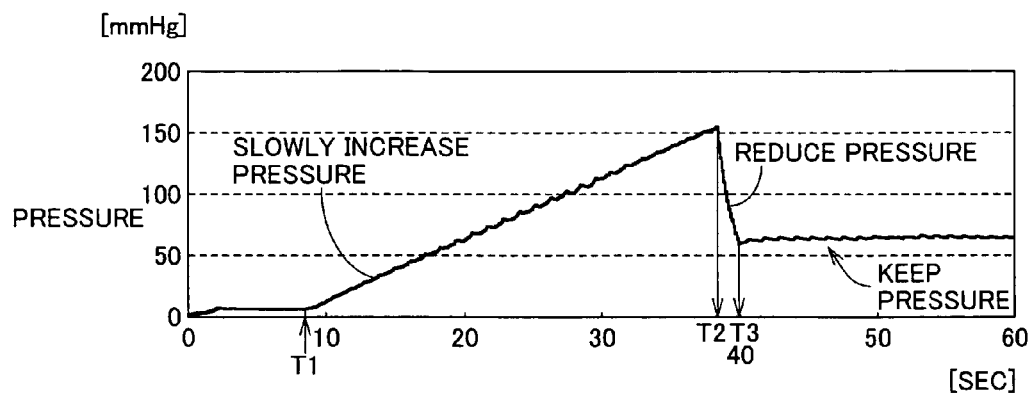
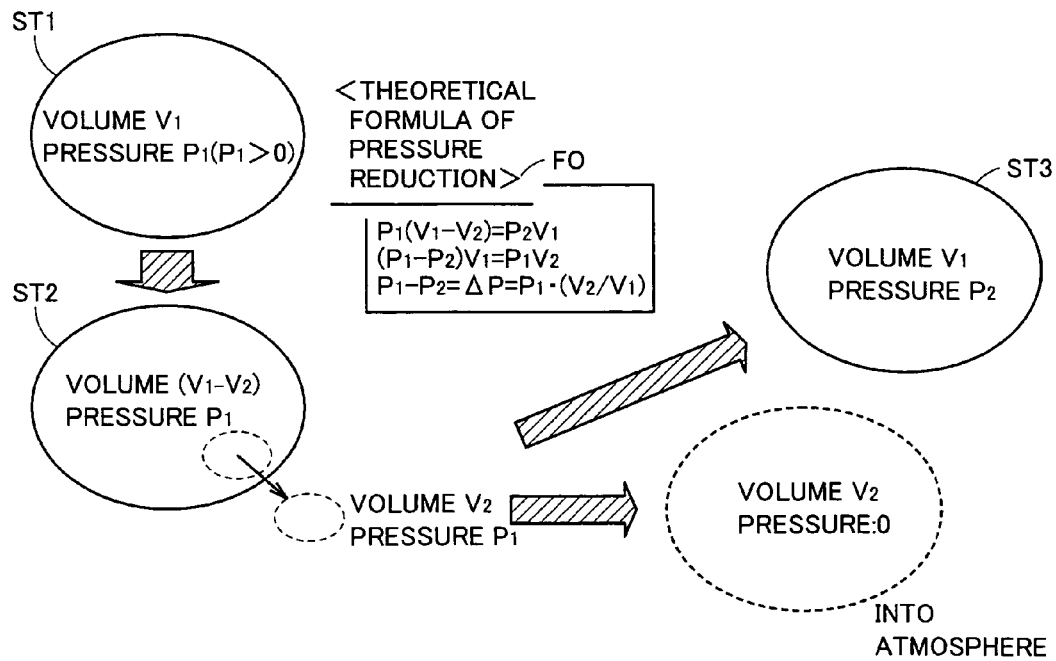

PRESSURE IS APPLIED

PRESSURE IS MAINTAINED

PRESSURE IS REDUCED

PRESSURE IS QUICKLY REDUCED

PULSE WAVE MEASURING APPARATUS

BACKGROUND OF THE INVENTION

1. Field of the Invention

The present invention relates to a pulse wave measuring apparatus for measuring changes in intra-arterial pressure by pressing a sensor against an artery with an appropriate pressure. In particular, the present invention relates to a pulse wave measuring apparatus controlling the internal pressure of an air bag used for pressurizing the artery, by supplying air into the air bag (increasing the pressure) or exhausting air from the air bag (reducing the pressure).

2. Description of the Background Art

Pressure wave generated as the heart beats and propagated through an artery or vibrations of the artery wall is/are generally called pulse wave. A pulse wave measuring apparatus has a sensor pressed against the surface of a measurement site of a subject's body in order to measure the pulse wave from an artery of the measurement site. For this purpose, the sensor has to be pressed against the subject's body with an appropriate pressure. When the sensor is pressed against the subject's body with an inappropriate pressure, the accuracy of the waveform of the pulse wave is deteriorated.

A pressing mechanism for pressing a sensor against a subject's body is disclosed for example in Japanese Patent Laying-Open No. 63-293424 which also discloses a pulse wave measuring apparatus including a pressure sensor for detecting the pulse wave, an air bag for pressing the pressure sensor against a subject's body, and a valve for adjusting the internal pressure of the air bag. The internal pressure of the air bag is adjusted by applying a drive signal to the valve.

A structure for adjusting the pressure by controlling supply of the air into the air bag or exhaustion of the air therefrom generally includes an air supply pump and a very-slow exhaust valve or quick exhaust valve that are employed in sphygmomanometers for example. The site of the subject's body to which the pressure is applied for measuring the pulse wave may be smaller in area than the site where the pressure is applied for measuring the blood pressure. Therefore, the air bag of the pulse wave measuring apparatus as well as the capacity thereof for keeping air are smaller than those of sphygmomanometers. It is thus extremely difficult to reduce, by minute amounts, the pressure in the air bag of the pulse wave measuring apparatus by exhausting the air at a very slow speed.

The sphygmomanometer measures the blood pressure by successively changing the internal pressure of the air bag, while the pulse wave measuring apparatus employs a control sequence as shown in FIG. 11A for applying the pressure. In FIG. 11A, the vertical axis represents the internal-pressure level of the air bag and the horizontal axis represents the passage of time. Further, FIG. 11B shows changes in output level of the pressure sensor as the internal pressure of the air bag is changed according to the sequence for applying the pressure. In FIG. 11B, the vertical axis represents the output level (pulse wave signal level) of the pressure sensor and the horizontal axis represents the passage of time corresponding to that shown in FIG. 11A.

Referring to FIG. 11A, pressurization is started at time T1, and the pressurization is continued until time T2 while searching for an optimum internal pressure level (pressurization level) which is a state herein called tonometry state. The optimum internal pressure level is an internal pressure level at which the amplitude of the waveform of the pulse wave obtained while the pressure is applied becomes constant.

In the period from the time when the pressurization is started to the time when the optimum internal pressure level is reached, the artery wall at the pressed site of the subject's body is curved by the pressing force, so that pressure applied (from the artery) to the pressure sensor increases due to influences of the tension of the curved artery wall. When the optimum internal pressure level is reached, the surface against which the sensor is pressed and the artery wall become almost in parallel with each other and accordingly, there is almost no influence of the tension of the artery wall on the vibrations of the artery perpendicular to the pressed surface. This state is the aforementioned tonometry state in which the pulse wave can accurately be detected.

At time T2, the internal pressure level is higher than the optimum internal pressure level. After time T2, the pressure is gradually reduced so that the determined optimum internal pressure level is reached. After time T3 at which the optimum internal pressure level is reached, the optimum internal pressure level is kept until the measurement is completed.

Referring to FIG. 11B, after the pressurization is started, the amplitude of the pulse wave signal gradually increases to become constant when the tonometry state is attained. As the pressurization is further continued, the bottom of the waveform of the pulse wave signal starts to distort. In the state where the optimum pressure level is maintained after time T3, the pulse wave is measured.

The control is effected by successively changing the internal pressure for determining the optimum internal pressure level and, after time T2 at which the internal pressure level exceeds the optimum internal pressure level, carrying out quick exhaustion (quick pressure reduction) and very-slow-speed exhaustion (very-slow-speed pressure reduction). Thus, in the short period between time T2 and T3, the pressure has to be reduced to the optimum internal pressure level and thereafter the optimum internal pressure level has to be maintained for a certain period of time until the measurement is completed. Accordingly, it has been a demand for a pressure control system having the functions of the quick exhaustion, very-slow-speed exhaustion and pressure maintenance.

Such a pressure control system is achieved for example by a syringe pump. The syringe pump is a device that finely controls the amount of air injected into a syringe which is a closed vessel or the amount of air discharged from the syringe by means of a stepping motor. A pulse wave measuring apparatus having the syringe pump mounted thereon cannot be reduced in size due to a large-sized control mechanism of the syringe pump and is not cost-effective because the syringe pump is expensive. In addition, when the pulse wave measuring apparatus having the syringe pump mounted thereon causes pain, due to pressurization, to a subject whose pulse wave is being measured, or when an emergency arises due to electric power failure for example, quick exhaustion of the syringe pump is difficult. Then, in order to address such a situation, a pump has to be added to the exterior for rapid exhaustion. It is seen from the above that, in order to mount the syringe pump on the pulse wave measuring apparatus and then satisfy functions required for measuring the pulse wave, various problems have to be solved.

SUMMARY OF THE INVENTION

An object of the present invention is to provide a pulse wave measuring apparatus that can simply adjust the level of the applied pressure.

According to an aspect of the present invention with the purpose of achieving the above-described object, a pulse wave measuring apparatus includes a pressure sensor pressed above an artery of a subject body, a pressing unit for applying pressure to the pressure sensor, and a pulse wave measuring unit for measuring pulse wave generated from the artery based on pressure information output from the pressure sensor in a process of changing the level of the pressure applied by the pressing unit to the pressure sensor.

The pressing unit includes a pressure adjusting unit having a gas container of a constant capacity for adjusting the level of the pressure applied to the pressure sensor using pressure of gas in the gas container, and a state changing unit.

The state changing unit sets the pressure adjusting unit to a gas holding state for holding an amount of the gas in the gas container, changes the gas holding state to a gas isolating state for isolating a partial amount of the gas held in the gas container in the gas holding state from the remaining amount of the gas, changes the gas isolating state to a gas discharging state for discharging the partial amount of the gas in the gas container that is isolated in the gas isolating state, and changes the gas discharging state to the gas holding state for holding the remaining amount of the gas in the gas container.

The state of the pressure adjusting unit which adjusts the level of the pressure applied to the pressure sensor is thus changed by the state changing unit through the gas holding state, the gas isolating state, the gas discharging state and the gas holding state in this order. In this process of the transition of the state, the amount of the gas originally in the gas container is decreased by the partial amount of the gas which is discharged, so that the pressure of the gas in the gas container is reduced. The level of the pressure applied to the pressure sensor can thus be adjusted easily merely by changing the state of the pressure adjusting unit in the state transition process.

Further, the state transition is repeated. Each time the state transition is made, a partial amount of the gas is discharged. Thus, the pressure applied to the pressure sensor can be reduced by the amount of pressure corresponding to the partial amount of the gas discharged in each state transition. The amount of pressure corresponding to the partial amount of the gas is for example 2 mmHg.

Preferably, the gas container includes an isolation unit keeping the partial amount of the isolated gas, a main unit except for the isolation unit, and a gas flow adjustment unit adjusting a gas flow passage between the main unit and the isolation unit. The state changing unit controls the gas flow adjustment unit in the gas holding state for establishing the gas flow passage and controls the gas flow adjustment unit in the gas isolating state and the gas discharging state for shutting off the gas flow passage.

The flow passage between the main unit and the isolation unit is thus shut off in the gas isolating state and the gas discharging state. Therefore, it is ensured that only the partial amount of the gas is isolated from the remaining amount of the gas and that only the partial amount of the gas is discharged. In this way, the level of the applied pressure can accurately be adjusted.

Preferably, the gas container includes an adjustment valve adjusting a gas flow passage between the isolation unit and atmosphere. The state changing unit controls the adjustment valve in the gas holding state and the gas isolating state for shutting off the gas flow passage between the isolation unit and the atmosphere and controls the adjustment valve in the gas discharging state for establishing the gas flow passage between the isolation unit and the atmosphere.

The gas flow passage between the isolation unit and the atmosphere is provided for discharging a partial amount of the gas and this flow passage is adjusted by the adjustment valve. While the adjustment valve establishes the gas flow passage between the isolation unit and the atmosphere in the gas discharging state, the adjustment valve shuts off the gas flow passage in the gas holding state and the gas isolating state.

The gas in the gas container is thus prevented from leaking into the atmosphere in the gas holding state so that the level of the applied pressure can be kept.

Preferably, the state changing unit sets the pressure adjusting unit to a gas supplying state for supplying gas to the gas container. The pressure adjusting unit further includes a supply source for supplying gas to the gas container in the gas supplying state.

The state of the pressure adjusting unit can further be changed to the gas supplying state. Then, the pressure adjusting unit can serve to keep, reduce and increase the level of the applied pressure.

Preferably, the gas flow adjustment unit is a three-port valve having a main-unit-related port for input/output of gas from/to the main unit, an isolation-unit-related port for input/output of gas from/to the isolation unit and a supply-related port for input of gas from the supply source. The state changing unit controls the three-port valve for connecting the main-unit-related port to the isolation-unit-related port in establishing the flow passage, and controls the three-port valve for connecting the main-unit-related port to the supply-related port in shutting off the flow passage and in the gas supplying state.

The above-described state transition can be made merely by changing the connection between the three ports of the three-port valve (gas flow adjustment unit).

Preferably, the state changing unit variably adjusts the period of the gas discharging state in changing the state from the gas discharging state to the gas holding state.

The period of time consumed in the gas discharging state can be made longer to completely discharge the partial amount of the gas of the isolation unit and thereby reduce the pressure by the amount corresponding to the partial amount of the gas. When this period of time is made relatively shorter, the state can be changed to the gas holding state before the partial amount of the gas is completely discharged, namely before the pressure is reduced by the amount corresponding to the partial amount of the gas. Thus, this period of time can variably be adjusted to variably adjust the amount of pressure by which the applied pressure is reduced. The level of the applied pressure can accordingly be adjusted precisely.

According to another aspect of the present invention, a pulse wave measuring apparatus includes a pressure sensor pressed above an artery of a subject body, a pressing unit for applying pressure to the pressure sensor, and a pulse wave measuring unit for measuring pulse wave generated from the artery based on pressure information output from the pressure sensor in a process of changing the level of the pressure applied by the pressing unit to the pressure sensor.

The pressing unit includes a pressure adjusting unit having a gas container of a constant capacity for adjusting the level of the pressure applied to the pressure sensor using pressure of gas in the gas container, and a state changing unit. The state changing unit sets the pressure adjusting unit to a gas holding state for holding an amount of the gas in the gas container, changes the gas holding state to a gas isolating and discharging state for isolating and discharging a partial amount of the gas held in the gas container in the gas holding state from the remaining amount of the gas, and changes the gas isolating and discharging state to the gas holding state for holding the remaining amount of the gas in the gas container.

The state of the pressure adjusting unit which adjusts the level of the pressure applied to the pressure sensor is thus changed by the state changing unit through the gas holding state, the gas isolating and discharging state, and the gas holding state in this order. In this process of the transition of the state, the amount of the gas originally in the gas container is decreased by the partial amount of the gas which is discharged, so that the pressure of the gas in the gas container is reduced. The level of the pressure applied to the pressure sensor can thus be adjusted easily merely by changing the state of the pressure adjusting unit in the state transition process.

Further, the state transition is repeated. Each time the state transition is made, a partial amount of the gas is discharged. Thus, the pressure applied to the pressure sensor can be reduced by the amount of pressure corresponding to the partial amount of the gas discharged in each state transition. The amount of pressure corresponding to the partial amount of the gas is for example 2 mmHg.

Preferably, the gas container includes an isolation unit keeping the partial amount of the isolated gas, a main unit except for the isolation unit, and a gas flow adjustment unit adjusting a gas flow passage between the main unit and the isolation unit. The state changing unit controls the gas flow adjustment unit in the gas holding state for establishing the gas flow passage and controls the gas flow adjustment unit in the gas isolating and discharging state for shutting off the gas flow passage.

The flow passage between the main unit and the isolation unit is thus shut off in the gas isolating and discharging state. Therefore, it is ensured that only the partial amount of the gas is isolated from the remaining amount of the gas and discharged. In this way, the level of the applied pressure can accurately be adjusted.

Preferably, the state changing unit sets the pressure adjusting unit to a gas supplying state for supplying gas to the gas container, and the pressure adjusting unit further includes a supply source for supplying gas to the gas container in the gas supplying state.

The state of the pressure adjusting unit can further be changed to the gas supplying state. Then, the pressure adjusting unit can serve to keep, reduce and increase the level of the applied pressure.

Preferably, the gas flow adjustment unit is a three-port valve having a main-unit-related port for input/output of gas from/to the main unit, an isolation-unit-related port for input/output of gas from/to the isolation unit and an atmosphere-related port leading to atmosphere. The state changing unit controls the three-port valve for connecting the isolation-unit-related port to the main-unit-related port in establishing the flow passage, and controls the three-port valve for connecting the isolation-unit-related port to the atmosphere-related port in shutting off the flow passage.

The above-described state transition can be made merely by changing the connection between the three ports of the three-port valve (gas flow adjustment unit).

Preferably, the isolation unit has a supply-related port for input of gas from the supply source in the gas supplying state, and the state changing unit controls the three-port valve in the gas supplying state for connecting the isolation-unit-related port to the main-unit-related port.

The state can thus be changed to the gas supplying state merely by changing the connection between three ports of the three-port valve (gas flow adjustment unit).

Preferably, the state changing unit variably adjusts the period of the gas isolating and discharging state in changing the state from the gas isolating and discharging state to the gas holding state.

The period of time consumed in the gas isolating and discharging state can be made longer to completely discharge the partial amount of the gas of the isolation unit and thereby reduce the pressure by the amount corresponding to the partial amount of the gas. When this period of time is made relatively shorter, the state can be changed to the gas holding state before the partial amount of the gas is completely discharged, namely for reducing the pressure by less than the amount corresponding to the partial amount of the gas. Thus, this period of time can variably be adjusted to variably adjust the amount of pressure by which the applied pressure is reduced. The level of the applied pressure can accordingly be adjusted precisely.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 4 is a graph showing changes in level of pressure applied to a pressure sensor when pulse wave is measured in the embodiment of the present invention.

FIG. 5 illustrates a theory of pressure reduction in the embodiment of the present invention.

DESCRIPTION OF THE PREFERRED EMBODIMENTS

An embodiment of the present invention is hereinafter described with reference to the drawings. It is noted that the capacity of some components each or the amount of decreased pressure are exemplary ones and the present invention is not limited thereto.

Figure 2:
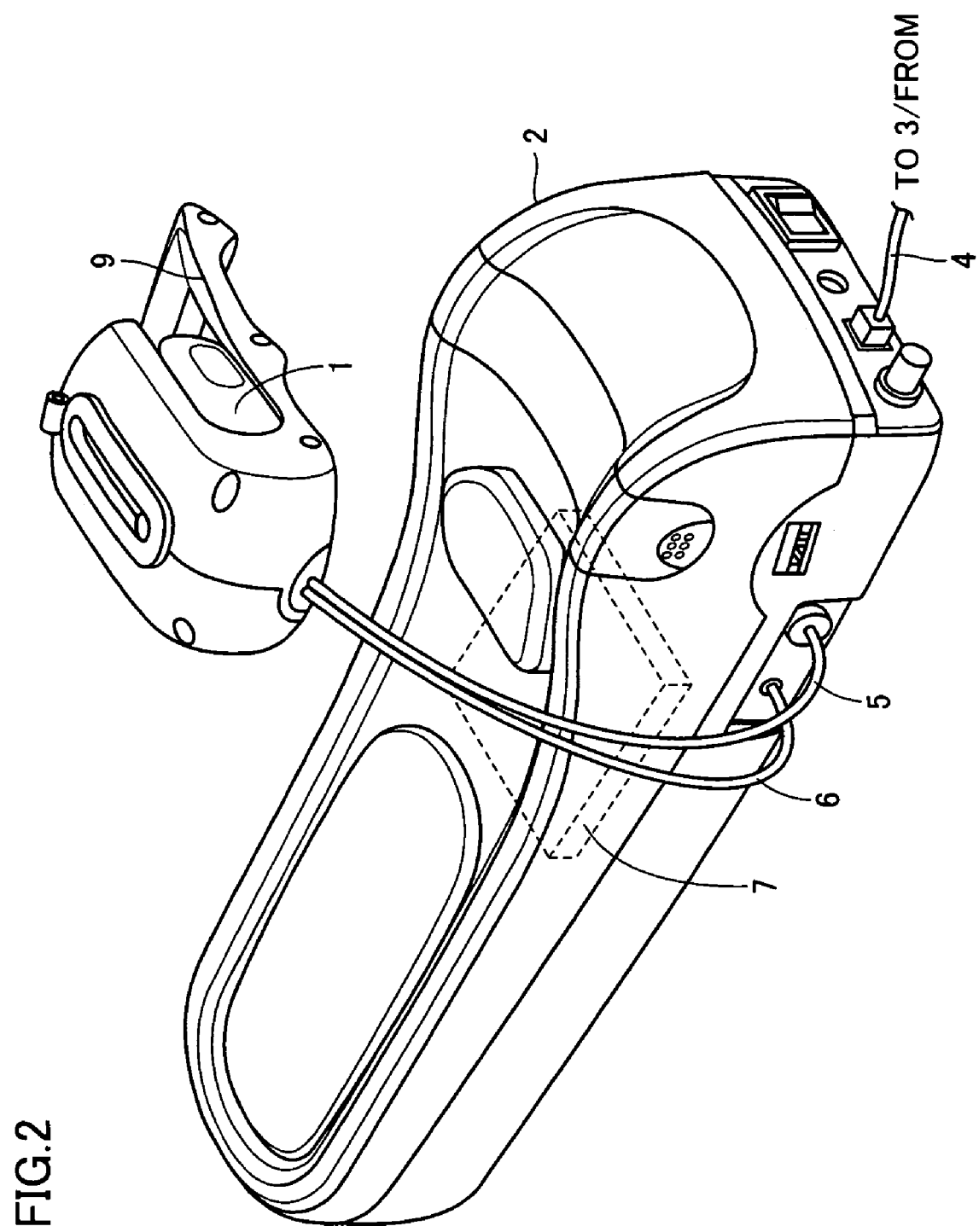
FIG. 2 shows how a sensor unit and a wrist rest are connected.
Figure 3:
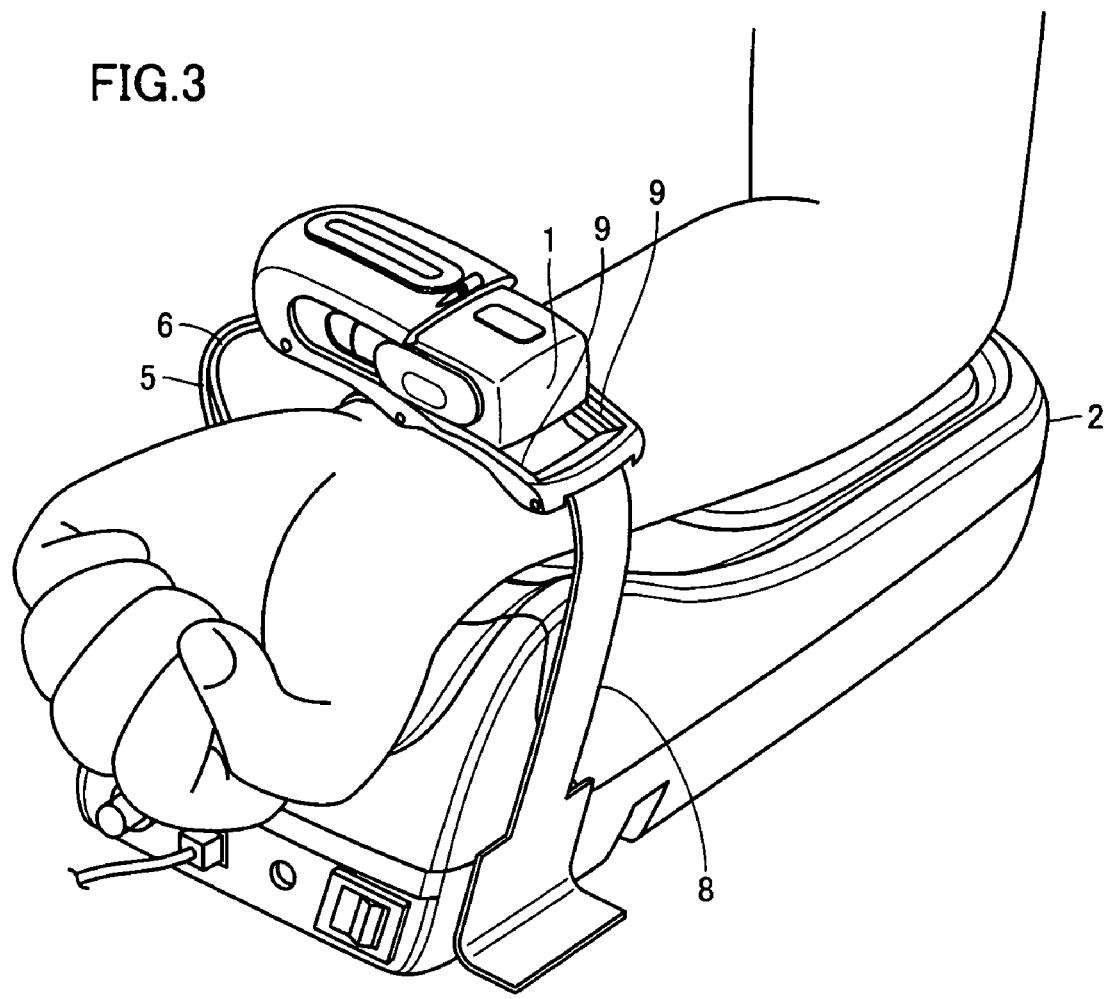
FIG. 3 shows a state in which the pulse wave measuring apparatus is mounted on a subject's body.

Referring to FIGS. 2 and 3, a pulse wave measuring apparatus for detecting the pulse wave of an artery of a wrist includes a sensor unit 1 mounted on the surface of the wrist, a wrist rest 2 to which the wrist is secured for detecting the pulse wave, and a PC (Personal Computer) unit 3 (not shown) for performing various operations including operations for detecting the pulse wave. FIG. 2 shows that sensor unit 1 is housed in a case and FIG. 3 shows that sensor unit 1 is slid out of the case along slide grooves 9 (see FIG. 2) to be positioned on the wrist.

Wrist rest 2 includes a wrist rest unit 7 therein, and the wrist rest unit 7 and PC unit 3 are communicatively connected via a USB (Universal Serial Bus) cable 4. Further, wrist rest unit 7 and sensor unit 1 are connected via a communication cable 5 and an air tube 6.

When the pulse wave is to be measured, as shown in FIG. 3, a user with the wrist placed on a predetermined position of wrist rest 2 slides sensor unit 1 to position sensor unit 1 on a surface where an artery of the wrist is located and fastens a belt 8 to secure the case of sensor unit 1 to wrist rest 2, so that sensor unit 1 on the wrist does not move.

Figure 1:
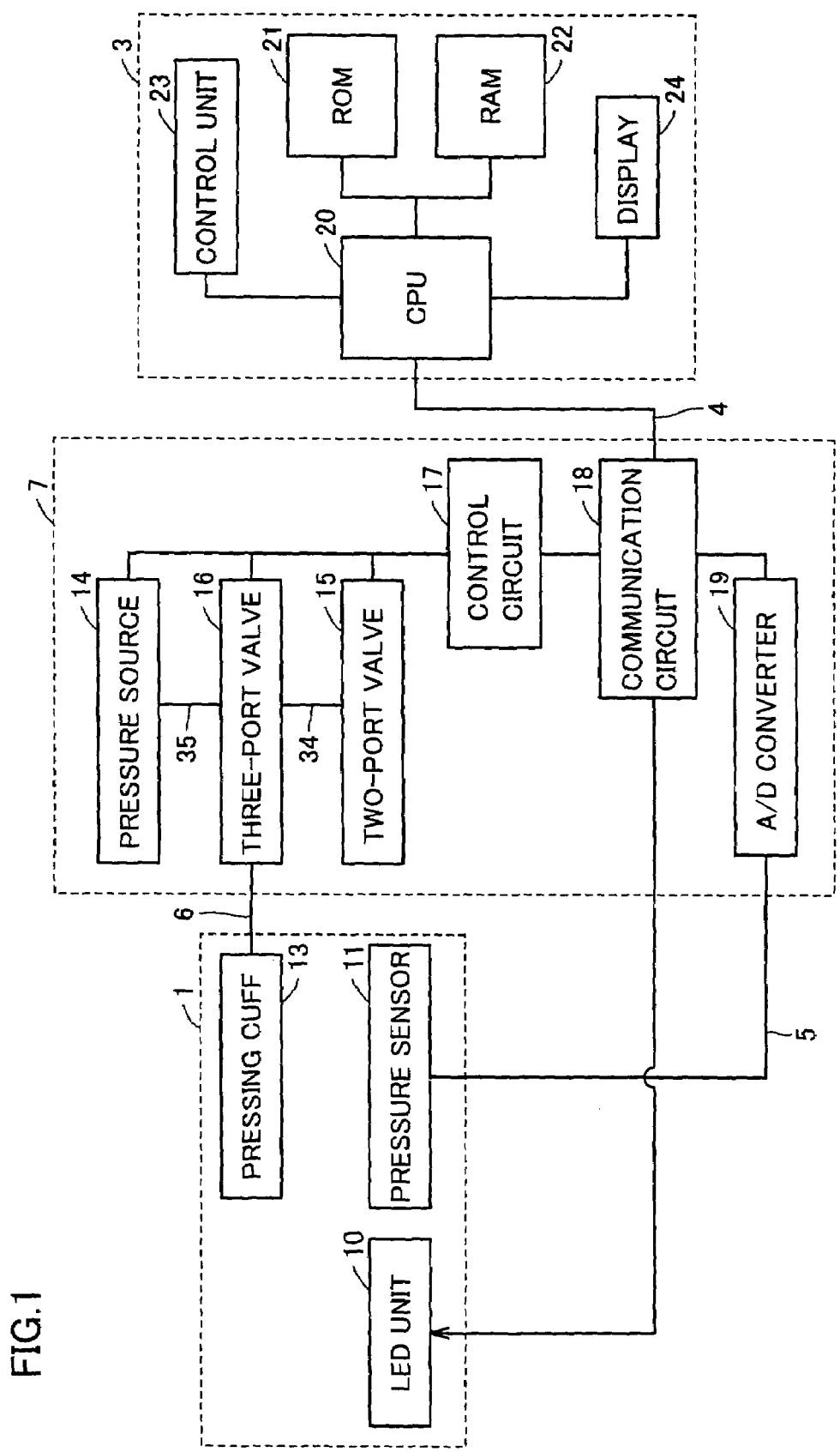
FIG. 1 is a functional diagram showing a structure of a pulse wave measuring apparatus according to an embodiment of the present invention.

Referring to FIG. 1, sensor unit 1 includes an LED unit 10 comprised of a plurality of LEDs (Light-Emitting Diodes) arranged in parallel with each other, LED unit 10 being placed to allow a light-emitting state thereof to be visible from the outside when mounted on the wrist, a pressure sensor 11, and a pressing cuff 13 with the pressurization adjusted for pressing pressure sensor 11 on the wrist. LED unit 10 is provided for informing the user, by means of the emitted light, of information for sliding sensor unit 1 (the position of the artery or the position of such a solid element as tendon for example). The medium for informing the user of the information is not limited to the LED and may be LCD (Liquid Crystal Display).

Wrist rest unit 7 includes a pressure source 14 comprised of a pressure pump for example for supplying air into pressing cuff (air bag) 13, a two-port valve 15 and a three-port valve 16 for adjusting the level of the pressure applied to pressure sensor 11 by means of the internal pressure of pressing cuff (air bag) 13, a control circuit 17 for controlling these elements, a communication circuit 18 to which USB cable 4 is connected, and an A/D (Analog/Digital) converter 19 for converting an output signal (pulse wave signal) from sensor unit 1 into digital data (pulse wave data). Three-port valve 16 selectively connects one of pressure source 14 and two-port valve 15 to air tube 6.

PC unit 3 includes a CPU (Central Processing Unit) 20 performing various operations including operations for centralized control of the pulse wave measuring apparatus, a ROM (Read-Only Memory) 21 and a RAM (Random-Access Memory) 22 storing data and program for controlling the pulse wave measuring apparatus, a control unit 23 provided so that it can be operated from the outside for entering information of various types, and a display 24 comprised of LCD for example for outputting such information as the measurements of the pulse wave to the outside.

Two-port valve 15 and three-port valve 16 are powered by a power supply (not shown), and CPU 20 controls the powering on and off of two-port valve 15 and three-port valve 16 through communication circuit 18 and control circuit 17.

Although wrist rest unit 7 of wrist rest 2 and PC unit 3 are separately provided here, both of them may be provided within wrist rest 2.

Figure 11A:
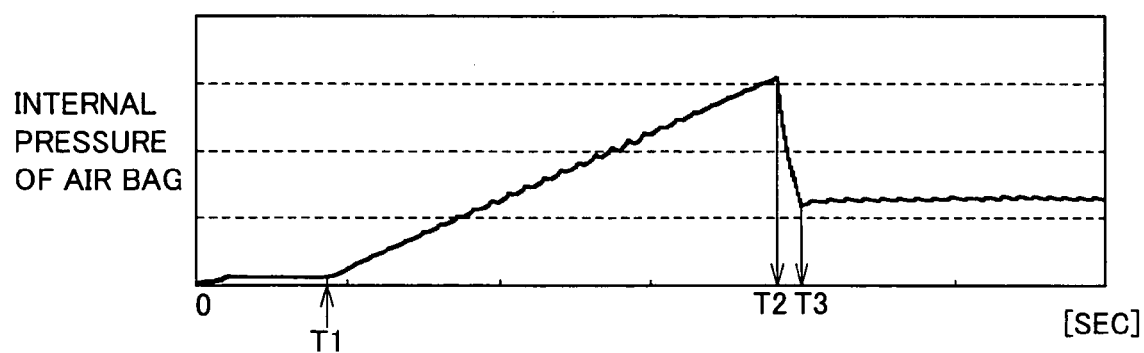
FIG. 11A and FIG. 11B illustrate a conventional pressurization sequence.

FIG. 4 shows changes in level of the pressure applied to pressure sensor 11 when the pulse wave is measured. In FIG. 4, the vertical axis represents the level of the applied pressure (mmHg) and the horizontal axis represents the passage of time. Referring to FIG. 4, the pressure is adjusted as illustrated in FIG. 11A. Specifically, in the state shown in FIG. 3, measurement is started at time T1. Then, pressure sensor 11 positioned right above an artery is pressed against a subject's body by increasing the internal pressure of pressing cuff 13. As the internal pressure of pressing cuff 13 is gradually increased by the pressure applied thereto, pressure sensor 11 pushes the artery against the radius so that the artery is becoming squeezed. When pressure sensor 11 is pressed against the subject's body with an optimum pressure, the artery is leveled (tonometry state) and accordingly the pulse wave generated from variations in intra-arterial pressure can accurately be measured. When the level of the pressure applied by pressing cuff 13 is further increased, the artery is further squeezed and eventually closed. In the above-described process, based on changes in waveform of a pulse wave signal detected by pressure sensor 11, CPU 20 determines the optimum pressure. When the measurement is taken, after time T2 at which the level of the applied pressure has been increased to exceed the optimum pressure, the level of the applied pressure is gradually reduced to the optimum pressure. After time T3 at which CPU 20 determines that the pressure is reduced to the optimum pressure, the optimum pressure is maintained. The pulse wave signal detected by pressure sensor 11 while the optimum pressure is maintained is converted by A/D converter 19 into pulse wave data. The pulse wave data is then provided to CPU 20 that performs such operations as calculation of an index on the data, and the results are indicated on display 24.

When the measurement is completed, the internal pressure of pressing cuff 13 is temporarily and quickly reduced to atmospheric pressure. Through the pressurization sequence as described above, the pulse wave measuring apparatus measures the pulse wave.

The level of the applied pressure is reduced to the optimum pressure in a short period of time (from time T2 to time T3). In this short period, the level of the applied pressure is reduced by several tens of mmHg and further reduced by a few mmHg for setting the pressure to the optimum pressure. For this purpose, fine adjustment of the applied pressure is performed.

Referring to FIG. 5, the process of reducing the pressure in the period from time T2 to time T3 is described. In FIG. 5, states ST1-ST3 of pressing cuff 13 having a certain capacity (=volume V1) are represented by internal pressure P1 (or P2) of pressing cuff 13 and volume V1 of the air within pressing cuff (air bag) 13. It is supposed here that the state of pressing cuff 13 is state ST1 (volume V1 and pressure P1 (P1>0)) at time T2. In order to reduce the pressure, a part of the air is discharged from the air bag, namely the air (pressure P1) of volume V2 (V1>V2>0) is discharged into the atmosphere (state ST2). The amount of air discharged to the atmosphere has volume V2, and the pressure of the discharged air becomes equal to zero (equal to atmospheric pressure). On the other hand, the state of the air bag changes from state ST2 to state ST3. In state ST3, the air of the amount left in the air bag is kept in the air bag (with its capacity equal to volume V1). Thus, the pressure of the air in the air bag changes to pressure P2 (<P1). In this state, as compared with state ST1, the internal pressure, namely the pressure applied to pressure sensor 11 is reduced by difference $\Delta P$ (=P1−P2). In this way, the transition of the state, i.e., ST1, ST2, ST3, ST1, ST2 . . . is repeated so that the internal pressure can gradually be reduced. FIG. 5 shows theoretical formula F0 of the reduction of the pressure in the above-described process of reducing the pressure.

Here, pressure P1 is 100 mmHg and difference $\Delta P$ is 2 mmHg for example. The value of difference $\Delta P$ is adjustable each time the state changes to state ST2. Thus, the fine adjustment of the cuff pressure in the pressure reduction process from time T2 to time T3 is facilitated.

Figure 6A:
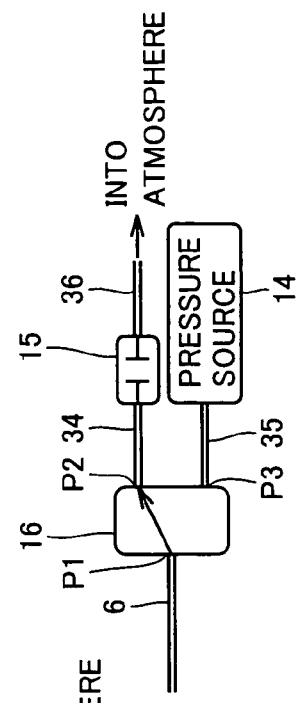
FIGS. 6A to 6D illustrate a basic structure in the embodiment of the present invention.

The control illustrated in FIGS. 4 and 5 is implemented under program control by CPU 20 of the mechanism comprised of pressure source 14, two-port valve 15 and three-port valve 16 as shown in FIGS. 6A-6D. Referring to FIG. 6A, pressing cuff 13 presses pressure sensor 11 against a surface of a subject's body 31 to pressurize an artery 32 at the pressed site within the body. The pulse wave of artery 32 generated by this pressurization is detected by pressure sensor 11. Pressing cuff 13 has one side on which pressure sensor 11 is mounted and the other side to which a member 33 for fixing and supporting pressing cuff 13 at an appropriate site is attached. To a first port P1 of three-port valve 16, pressing cuff 13 is connected via air tube 6. To a second port P2 thereof, one port of two-port valve 15 is connected via an air tube 34. To a third port P3 thereof, pressure source 14 is connected via an air tube 35. The other port of two-port valve 15 is connected to an air tube 36 extending into the atmosphere.

Figure 6C:
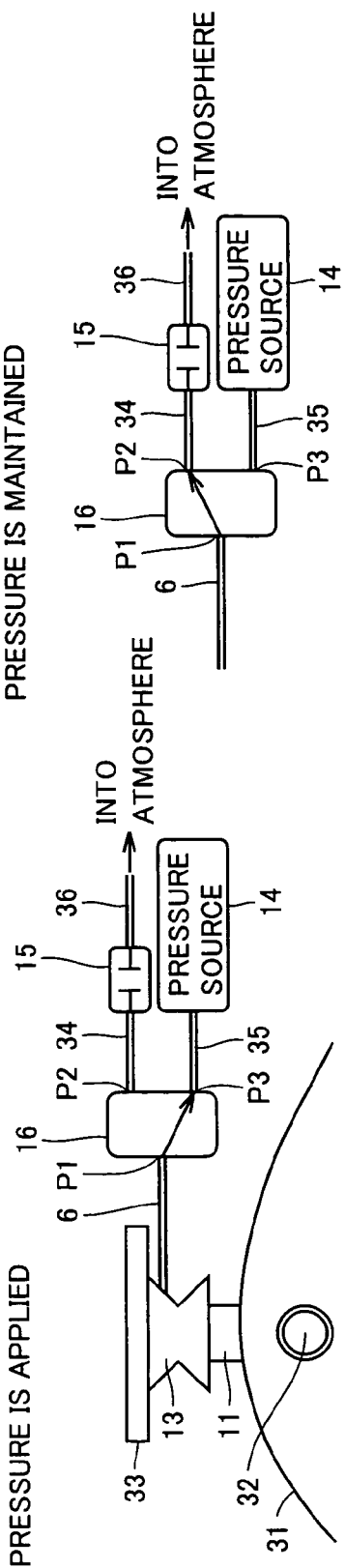
Figure 6B:
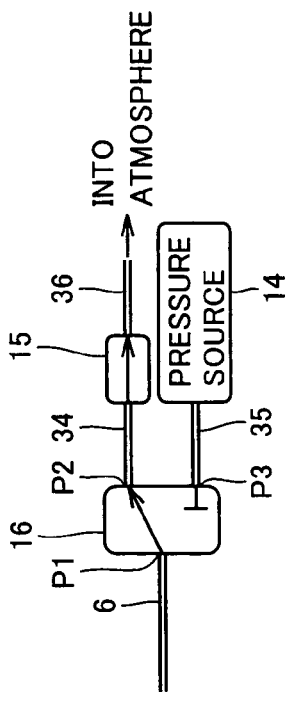
Figure 6D:
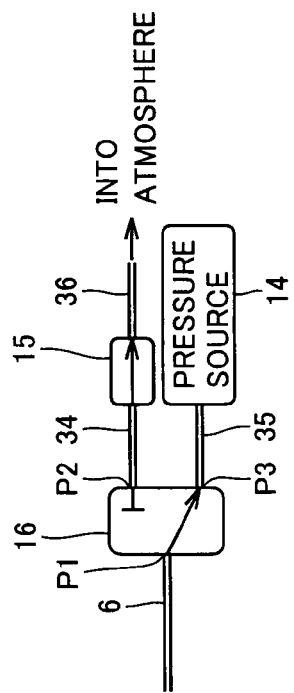

When supply of current to three-port valve 16 is stopped (three-port valve 16 is powered off) by CPU 20, three-port valve 16 changes the connection so that first and second ports P1 and P2 are connected to each other (see FIGS. 6C and 6D). Accordingly, a flow passage of air is established by air tubes 6 and 34 and three-port valve 16 between pressing cuff 13 and two-port valve 15. At this time, three-port valve 16 and air tube 34 hold air of 0.2 to 0.3 ml. In contrast, when current is supplied to three-port valve 16 (three-port valve 16 is powered on) by CPU 20, the connection is changed so that first and third ports P1 and P3 are connected to each other (see FIGS. 6A and 6B). Accordingly, the flow passage between pressing cuff 13 and two-port valve 15 is shut off. In other words, a flow passage of air is established by air tubes 6 and 35 and three-port valve 16 between pressing cuff 13 and pressure source 14 instead of the above-described flow passage.

When supply of current to two-port valve 15 is stopped (two-port valve 15 is powered off) by CPU 20, two-port valve 15 is opened (see FIGS. 6B and 6D). Thus, air tubes 34 and 36 are connected by two-port valve 15 so that a flow passage of air is established by air tubes 34 and 36 and two-port valve 15. In contrast, when current is supplied to two-port valve 15 (two-port valve 15 is powered on) by CPU 20, two-port valve 15 is closed (see FIGS. 6A and 6C) and the air flow passage is accordingly shut off by two-port valve 15.

When a pressure pump for example of pressure source 14 is driven according to an instruction from CPU 20 and accordingly air is supplied via three-port valve 16 to pressing cuff 13, the internal pressure of pressing cuff 13 increases. A valve (not shown) is provided at the joint where pressure source 14 and air tube. 35 contact each other for preventing, by the valve, the air from flowing from air tube 35 into pressure source 14.

The pressure applied to pressure sensor 11 corresponds to the pressure of the air held by pressing cuff 13, air tubes 6 and 35 and three-port valve 16 in the state shown in FIG. 6A, corresponds to the pressure of the air held by pressing cuff 13, air tubes 6 and 3 5 and three-port valve 16 in the state shown in FIG. 6B, and corresponds to the pressure of the air held by pressing cuff 13, air tubes 6 and 34 and three-port valve 16 in the state shown in FIG. 6C.

Figure 7B:
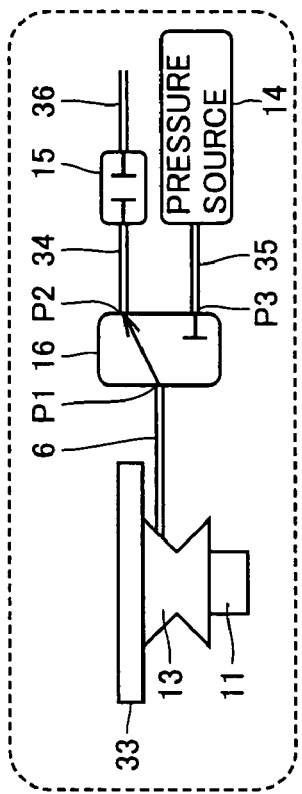
FIGS. 7A to 7D illustrate in detail a process of reducing pressure in the embodiment of the present invention.
Figure 7C:
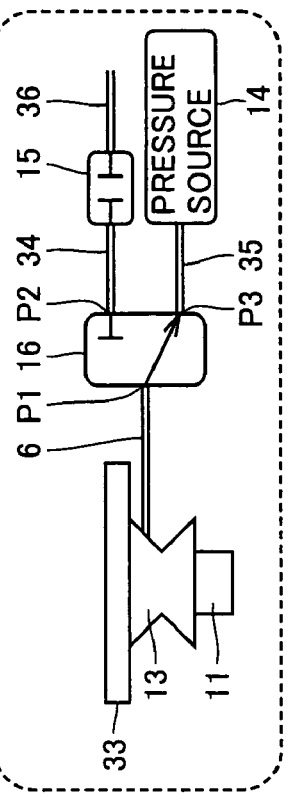
Figure 7D:
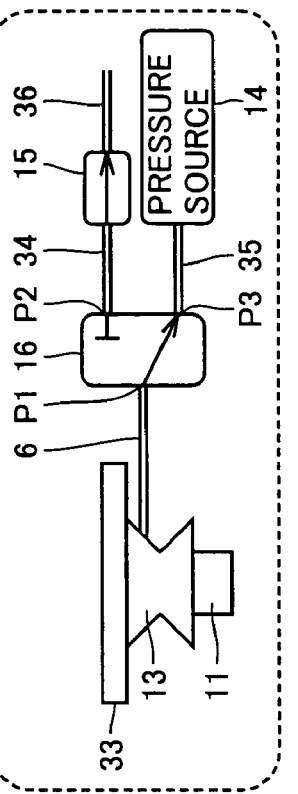
Figure 7A:

Referring to FIGS. 6A-6D and FIGS. 7A-7D, a procedure for controlling the mechanism comprised of pressure source 14, two-port valve 15 and three-port valve 16 according to the sequence shown in FIG. 4 is described. FIG. 7A is a graph showing in detail the process of reducing pressure in the period from time T2 to time T3 shown in FIG. 4. The vertical axis represents the level of pressure applied to pressure sensor 11 and the horizontal axis represents the passage of time.

Figure 11B:
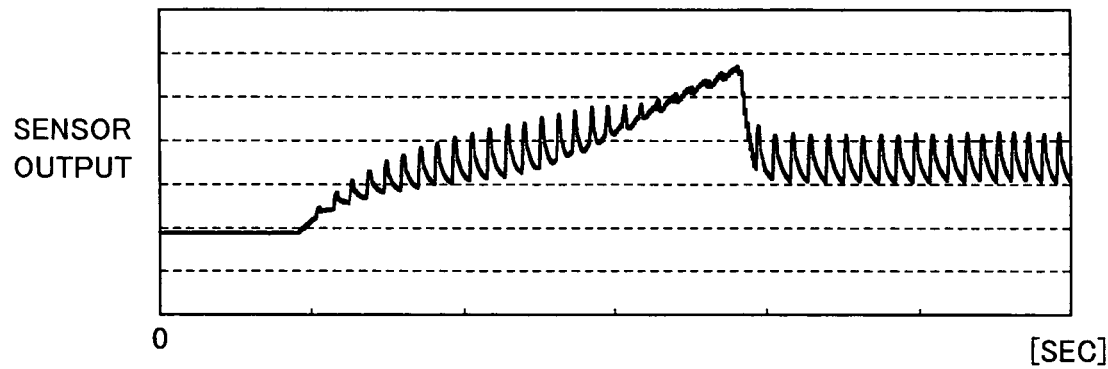

When the pressure is increased slowly in the period from time T1 to time T2 shown in FIG. 4, the air flow passage as shown in FIG. 6A is established and pressure source 14 is driven. Air is thus injected into pressing cuff 13 and the internal pressure increases slowly as the amount of pressure injected into pressing cuff 13 increases. In the period in which the level of the pressure applied to pressure sensor 11 including the internal pressure increases, an optimum pressure is searched for. This searching procedure is the same as that described in connection with FIGS. 11A and 11B. Then, when the applied pressure exceeds the optimum pressure (time T2), CPU 20 stops driving pressure source 14 and stops supply of current to three-port valve 16 (powers off three-port valve 16) (see FIGS. 6C and 7B). Accordingly, the air in the air holding portion comprised of the established flow passage and the air bag of pressing cuff 13 for example is temporarily held therein to keep the level of the pressure applied to pressure sensor 11.

The process of reducing pressure (from time T2 to time T3) is thereafter followed. Specifically, three-port valve 16 is powered on to isolate pressing cuff 13 and air tube 6 from the air passage which is established for the purpose of reducing pressure (discharging air), namely from air tube 34 (see FIG. 7C). In this state, the air in three-port valve 16 and the air in air tube 34 correspond to a part of the air contained in the air holding portion shown in FIGS. 6C and 7B while the air in pressing cuff 13 and the air in air tube 6 correspond to the remainder thereof The reminder of the air is held in an air keeping portion (comprised of pressing cuff 13, air tubes 6 and 35 and three-port valve 16).

Then, two-port valve 15 is powered off (see FIGS. 6B and 7D). Accordingly, the part of the air (0.2-0.3 ml) held in three-port valve 16 and air tube 34 is discharged to the atmosphere via two-port valve 15 while the reminder of the air after the discharge is held in the air keeping portion (comprised of pressing cuff 13, air tubes 6 and 35 and three-port valve 16). Thus, the pressure applied to pressure sensor 11 is reduced by approximately 2 mmHg. After this, two-port valve 15 is powered on (see FIG. 7C), three-port valve 16 is powered off (see FIGS. 6C and 7B), and the level of pressure after reduced (corresponding to the reminder of the air) is kept.

The pressure reduction mechanism is thus achieved through the process of transition of the state shown in FIG. 7C, FIG. 7D, FIG. 7C, FIG. 7B in this order. In this process, a part of the air held for applying the pressure to pressure sensor 11 is isolated and discharged, and the reminder of the air is thereafter released to the space of the volume (capacity) corresponding to the portion originally holding the air (comprised of pressing cuff 13, air tubes 6 and 34, three-port valve 16 and two-port valve 15).

The pressure applied to pressure sensor 11 is controlled by switching of three-port valve 15 and two-port valve 16. Accordingly, the switch of the state is implemented from the state of holding the air, the state of isolating the air, the state of discharging the air and the state of holding the air in this order. In this way, the pressure applied to pressure sensor 11 can easily be reduced by a very small amount. Further, this process of transition of the state can be repeated to repeatedly reduce the pressure by a small amount. Here, for ease of description, the transition of the state shown in FIG. 7C, FIG. 7D, FIG. 7C in this order is referred to as "sequence SC".

In the period in which the level of the applied pressure kept after the sequence SC is followed is not the optimum pressure, namely in the period from time T 2 to time T3 shown in FIG. 4, the sequence SC is followed again and then the state changes to that shown in FIG. 6C (or FIG. 7B). Thus, the level of the pressure that has further been reduced is maintained. If the maintained pressure is the optimum pressure, the pulse wave is measured in the state shown in FIG. 6C (or FIG. 7B). Otherwise, the sequence SC is followed again for reducing the pressure in the same manner.

In this way, the sequence SC is repeated to reduce the pressure. When the pressure applied to pressure sensor 11 reaches the optimum pressure, namely at time T3 shown in FIG. 4, the state shown in FIG. 6C (or FIG. 7B) is kept while the pulse wave is measured at the optimum pressure. After the pulse wave is measured or an emergency instruction is given by external control upon occurrence of electric power failure for example, two-port valve 15 and three-port valve 16 are powered off (see FIG. 6D) to establish the air flow passage comprised of air tubes 6, 34 and 36, three-port valve 16 and two-port valve 15 for discharging the air held in pressing cuff 13 for example. Then, the air held therein is immediately discharged via the passage to the atmosphere. The pressure applied to pressure sensor 11 (artery 32) is thus quickly reduced to the level of atmospheric pressure.

In FIG. 7A, it is illustrated that the level of the pressure applied to pressure sensor 11 is reduced in step-wise manner by repeatedly following the sequence SC, the optimum pressure level is kept for measuring the pulse wave at time T3 (when the optimum pressure level is attained), and then, at time T4 (when the measurement of the pulse wave is completed), the state changes to the one shown in FIG. 6D so that the applied pressure is quickly reduced.

The repetition of the sequence SC allows the process of reducing the pressure in the period from T2 to T3 shown in FIG. 4 to be implemented. Here, the amount of the air that can be held in three-port valve 16 and air tube 34 is fixed. Therefore, the period of the state in FIG. 7D in changing the state from the state in FIG. 7D to that shown in FIG. 7C can be adjusted to adjust the amount of discharged air so that the amount of reduced pressure in each sequence SC can be made variable.

Figure 8:
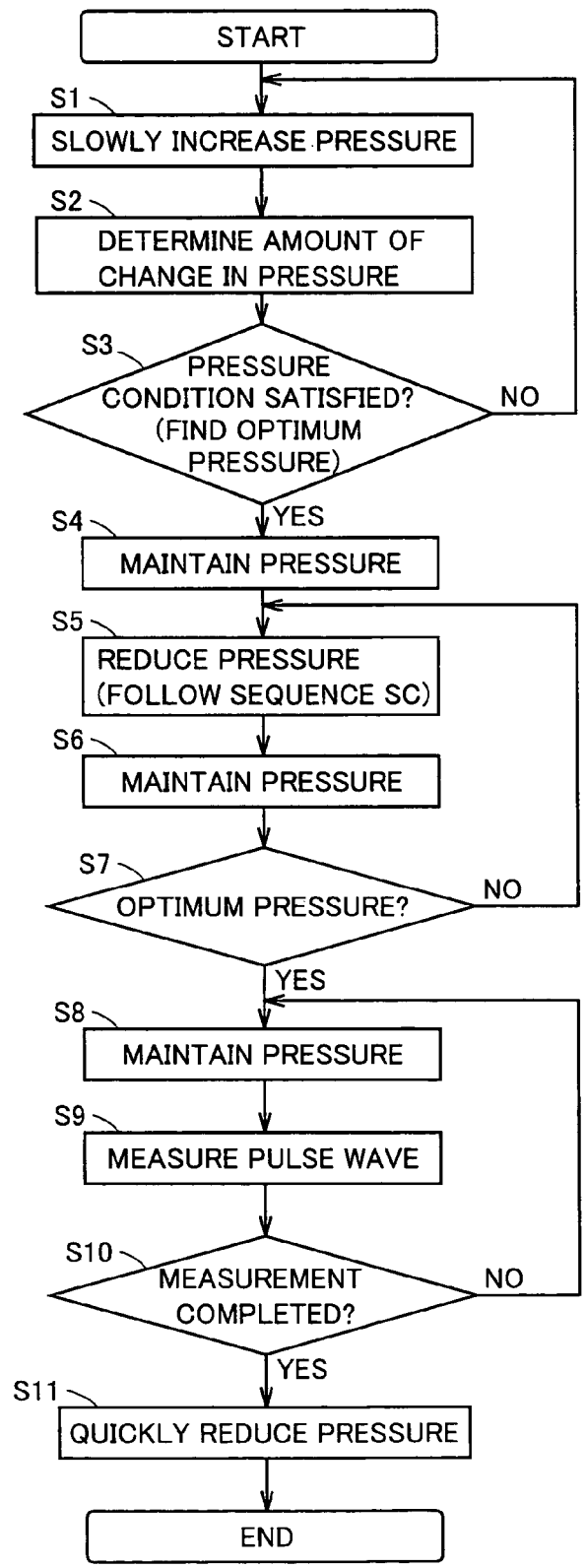
FIG. 8 is a flowchart of measurement of pulse wave in the embodiment of the present invention.

A procedure for measuring the pulse wave in this embodiment is described according to the flowchart shown in FIG. 8. A program following this flowchart and data used when the program is executed are stored in advance in ROM 21 or RAM 22. CPU 20 reads and executes the program while referring to the data as required, and accordingly, the process of adjusting the pressure applied to pressure sensor 11 and the process of measuring the pulse are carried out.

It is supposed here that it is now the state as shown in FIG. 3 in which the pulse wave can be measured. In the state shown in FIG. 3, a user turns on a power switch (not shown) and then CPU 20 gives an instruction to control circuit 17 via communication circuit 18 to start pressurization. Following this instruction, control circuit 17 drives pressure source 14 and powers on three-port valve 16 and two-port valve 15. Then, the state changes to the one shown in FIG. 6A so that air is gradually sent from pressure source 14 toward pressing cuff 13 and the internal pressure of pressing cuff 13 increases slowly (S1). Pressure sensor 11 thus pressurizes artery 32 of the wrist.

Then, for measuring the pulse wave, CPU 20 calculates the amount of change in level of the pressure applied to pressing cuff 13 (cuff pressure) based on information about pressure received from pressure sensor 11. Then, CPU 20 compares the calculated amount of change and a predetermined amount of change in the state in which the pulse wave can be detected (S2). The amount of change is calculated according to a known procedure. If the calculated amount of change meets the predetermined amount of change, it is determined that the condition of the applied pressure for detecting the pulse wave is satisfied (YES in S3). If not (NO in S3), the steps S2 and S3 are repeated until the condition of the applied pressure is satisfied.

When the condition of the applied pressure is satisfied (YES in S3, time T2 in FIG. 4), the pressure applied to pressure sensor 11 has its level higher than the optimum pressure level.

After this, CPU 20 gives an instruction to control circuit 17 via communication circuit 18 to change the state to the state of keeping the pressure shown in FIG. 6C. Then, control circuit 17 stops driving pressure source 14 and powers off three-port valve 16 (S4). The level of the pressure applied to pressure sensor 11 is thus maintained. After this, the process proceeds to the procedure of reducing pressure followed after time T2 in FIG. 4.

For changing the state to the process of reducing the pressure, CPU 20 gives an instruction to control circuit 17 via communication circuit 18 to follow the sequence SC. Then, control circuit 17 powers on/off two-port valve 15 and three-port valve 16 so that the sequence SC is carried out (S5). Accordingly, the level of the applied pressure is reduced. After this, CPU 20 gives an instruction to control circuit 17 via communication circuit 18 to change the state to the state of keeping the pressure shown in FIG. 6C. Control circuit 17 thus turns off three-port valve 16 (S6). The level of the applied pressure after reduced through the sequence SC is thus maintained. In this state, the information about pressure that is output from pressure sensor 11, namely data about the waveform of the pulse wave of artery 32, is transferred via A/D converter 19 and communication circuit 18 to CPU 20.

Receiving the waveform data, CPU 200 determines, based on whether or not the received waveform data matches the waveform in the tonometry state (namely having constant amplitude), whether the level of the applied pressure reaches the level of the optimum pressure for measuring the pulse wave (S7). This determination is made by storing in advance, in ROM 21 for example, data about the waveform of the pulse wave at the optimum pressure, and comparing this pressure with the received waveform data. If the pressure has not reached the optimum pressure (NO in S7), the process returns to S5 to further reduce the applied pressure. After this, steps S5 and S6 are repeated until the optimum pressure is attained (YES in S7).

When CPU 20 determines that the level of the applied pressure reaches the optimum pressure level (YES in S7), CPU 20 gives an instruction to control circuit 17 via communication circuit 18 to change she state to the state of keeping the pressure shown in FIG. 6C. Then, control circuit 17 powers off three-port valve (S8). The optimum pressure is thus maintained.

In this way, with the optimum pressure maintained, the pulse wave is measured (S9). Specifically, the information about pressure output from pressure sensor 11, i.e., data about the waveform of the pulse wave, is transferred via A/D converter 19 and communication circuit 18 to CPU 20. CPU 20 receiving the waveform data then follows the process for measuring the pulse wave based on the received waveform data. The process of measuring the pulse wave follows a known procedure and thus the detailed description thereof is not given here.

Until a predetermined condition for ending the measurement of the pulse wave is satisfied, steps S8 and S9 are repeated. When satisfied (YES in S10), CPU 20 gives an instruction to control circuit 17 via communication circuit 18 to change the state to the state of quickly reducing the pressure shown in FIG. 6D. Then, control circuit 17 powers off two-port valve 15 while three-port valve 16 is still powered off (S11). The state of pressurizing artery 32 by pressure sensor 11 is cancelled and accordingly the series of steps of the process for measuring the pulse wave are completed.

As discussed above, the sequence SC is repeated so that a slight amount of the air included in the air held in the state of keeping the pressure can repeatedly be discharged in step-wise manner. Therefore, even if the air bag of pressing cuff 13 has a small air capacity, the internal pressure (cuff pressure) can accurately be controlled for slowly reducing the pressure and for quickly reducing the pressure (discharging the air).

Here, the predetermined condition for ending the measurement of the pulse wave is for example input of an instruction from control unit 23 to end (stop) measurement, detection of electric power failure, completion of the process of obtaining required measurement data, for example.

CPU 20 outputs the information about the detected pulse wave to the outside through display 24 for example. CPU 20 may use the information about the pulse wave in calculating AI (Augmentation Index) to output the calculated AI.

Another Example of Structure

Figure 9:
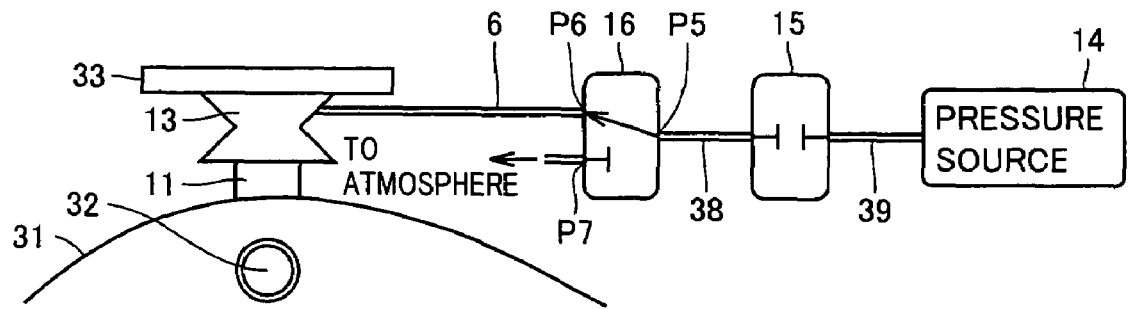
FIG. 9 shows another example of the structure in the embodiment of the present invention.

When it is unnecessary to carry out the process of quickly reducing the pressure shown in FIG. 6D for example, the structure as shown in FIG. 9 may be employed. Referring to FIG. 9, three-port valve 16 includes a port P6 for connection of air tube 6, a port P7 for connection of an air tube leading to the atmosphere, and a port P5 for connection of one end of an air tube 38. One port of two-port valve 15 connects the other end of air tube 38 and the other port thereof connects one end of an air tube 39. Pressure source 14 connects the other end of air tube 39. At the joint between pressure source 14 and air tube 39, a valve (not shown) is provided for preventing, by the valve, air from flowing from air tube 39 into pressure source 14.

When three-port valve 16 is powered off, three-port valve 16 changes the connection so that ports P5 and P6 are connected to each other. When three-port valve 16 is powered on, three-port valve 16 changes the connection so that ports P5 and P7 are connected to each other. When two-port valve 15 is powered off, two-port valve 15 is opened to establish an air flow passage comprised of air tubes 38 and 39 and two-port valve 15. When two-port valve 15 is powered on, two-port valve 15 is closed so that the air flow passage is shut off by two-port valve 15.

Respective operations of pressure source 14, two-port valve 15 and three-port valve 16 shown in FIG. 9 are controlled as well by CPU 20 through control circuit 17.

In operation, in the period from time T1 to time T2 shown in FIG. 4 in which the pressure is slowly increased, pressure source 14 is driven, three-port valve 16 is powered off and two-port valve 15 is powered on. Accordingly, air is sent from pressure source 14 toward pressing cuff 13 via air tubes 6, 38 and 39, three-port valve 16 and two-port valve 15. The pressure applied to pressure sensor 11 is thus increased.

At time T2, driving of pressure source 14 is stopped, three-port valve 16 is stilled powered off and two-port valve 15 is powered off. Accordingly, the applied pressure is maintained. Then, with two-port valve 15 powered off, three-port valve 16 is powered on so that a slight amount of air separately held in air tube 3 8 and three-port valve 16 is sent (discharged) into the atmosphere while the remaining amount of the air after the discharge is held in a holding portion (comprised of pressing cuff 13, air tube 6 and three-port valve 16). The applied pressure is thus reduced by a slight amount (see ΔP in FIG. 5). In order to maintain the pressure after reduced, two-port valve 15 is still powered off while three-port valve 16 is powered off. In this way, the reduction of the pressure by a slight amount (ΔP) is repeated until time T3 (until the optimum pressure is reached). When the optimum pressure is reached, the applied pressure is kept and the pulse wave is measured.

An example of the case where the process of quickly reducing the pressure is unnecessary as shown in FIG. 9 is the one where a pump is newly provided for quickly reducing the pressure applied to pressure sensor 11.

Still Another Example of Structure

Figure 10:
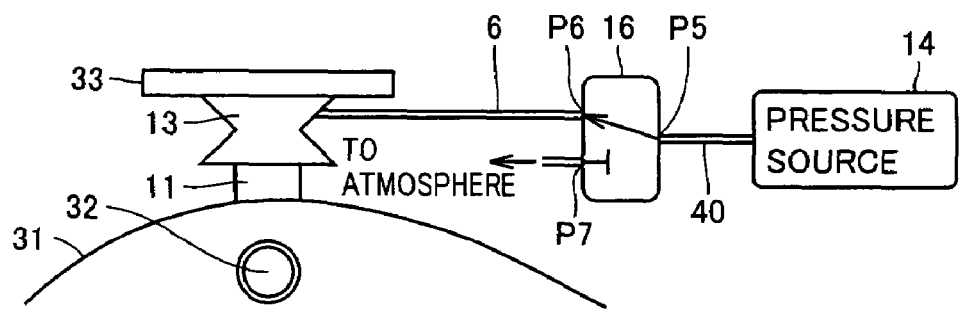
FIG. 10 shows still another example of the structure in the embodiment of the present invention.

When the process of quickly reducing the pressure as shown in FIG. 6D is unnecessary and the pressure can be maintained by means of pressure source 14, the structure shown in FIG. 10 may be employed.

Referring to FIG. 10, three-port valve 16 includes a port P6 for connection of air tube 6, a port P7 for connection of an air tube leading to the atmosphere and a port P5 for connection of one end of an air tube 40. Pressure source 14 connects the other end of air tube 40. At the joint between pressure source 14 and air tube 40, a valve (not shown) is provided for preventing, by the valve, the air from flowing from air tube 40 into pressure source 14. In the structure shown in FIG. 10, two-port valve 15 is unnecessary.

When three-port valve 16 is powered off, three-port valve 16 changes the connection so that ports P5 and P6 are connected to each other. When three-port valve 16 is powered on, it changes the connection so that ports P5 and P7 are connected to each other.

Respective operations of pressure source 14 and three-port valve 16 shown in FIG. 10 are controlled as well by CPU 20 through control circuit 17.

In operation, in the period from time T1 to time T2 shown in FIG. 4 in which the pressure is slowly increased, pressure source 14 is driven and three-port valve 16 is powered off. Accordingly, air is sent from pressure source 14 toward pressing cuff 13 via air tubes 6 and 40 and three-port valve 16. The pressure applied to pressure sensor 11 is thus increased.

At time T2, three-port valve 16 is stilled powered off while driving of pressure source 14 is stopped. By the valve at the joint between pressure source 14 and air tube 40, flow of the air from air tube 40 into pressure source 14 is prevented. Thus, the applied pressure is maintained. Then, three-port valve 16 is powered on so that a slight amount of air separately held in air tube 40 and three-port valve 16 is sent (discharged) into the atmosphere while the remaining amount of the air after the discharge is held in a holding portion (comprised of pressing cuff 13, air tube 6 and three-port valve 16). The applied pressure is thus reduced by a slight amount (ΔP). In order to maintain the pressure after reduced, three-port valve 16 is powered off. In this way, the reduction of the pressure by a slight amount (ΔP) is repeated until time T3 (until the optimum pressure is reached). When the optimum pressure is reached, the applied pressure is kept and the pulse wave is measured.

When the mechanism shown in FIGS. 9 or 10 is provided to the pulse wave measuring apparatus shown in FIG. 1, other components are those as shown in FIG. 1.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A pulse wave measuring apparatus comprising:
   a pressure sensor that is configured to be pressed above an artery of a subject body;
   a pressing device configured for applying pressure to the pressure sensor;
   a pulse wave measuring unit configured for measuring pulse wave generated from the artery based on pressure information output from the pressure sensor in a process of changing the level of the pressure applied by the pressing device to the pressure sensor,
   the pressing device including:
   a gas container of a constant capacity for adjusting the level of the pressure applied to the pressure sensor using pressure of gas in the gas container, and
   a state changing unit setting the pressure of the gas container to a gas holding state for holding an amount of the gas, changing the gas holding state to a gas isolating state for isolating a partial amount of the gas held in the gas container in the gas holding state from the remaining amount of the gas, changing the gas isolating state to a gas discharging state for discharging the partial amount of the gas in the gas container that is isolated in the gas isolating state, and changing the gas discharging state to the gas holding state for holding the remaining amount of the gas in the gas container;

an isolation unit keeping the partial amount of the isolated gas;

a main unit;

a gas flow adjustment unit adjusting a gas flow passage between the main unit and the isolation unit, wherein a pressure adjusting unit further includes a supply source for supplying gas to the gas container in a gas supplying state;

wherein the state changing unit is configured for setting the pressure adjusting unit to the gas supplying state for supplying gas to the gas container;

wherein the state changing unit controls the three-port valve for connecting a main-unit-related port to the isolation-unit-related port in establishing the flow passage, and controls the three-port valve for connecting the main-unit-related port to a supply-related port in shutting off the flow passage and in the gas supplying state; and wherein the gas flow adjustment unit is a three-port valve having a main-unit-related port for input/output of gas from/to the main unit, an isolation-unit-related port for input/output of gas from/to the isolation unit and a supply-related port for input of gas from the supply source.

2. The pulse wave measuring apparatus according to claim 1, wherein said gas container includes an adjustment valve adjusting a gas flow passage between said isolation unit and atmosphere, and wherein said state changing unit controls said adjustment valve in said gas holding state and said gas isolating state for shutting off the gas flow passage between said isolation unit and said atmosphere and controls said adjustment valve in said gas discharging state for establishing the gas flow passage between said isolation unit and said atmosphere.

3. A pulse wave measuring apparatus comprising:

a pressure sensor configured to be pressed above an artery of a subject body;

a pressing device configured for applying pressure to said pressure sensor; and a pulse wave measuring unit configured for measuring pulse wave generated from said artery based on pressure information output from said pressure sensor in a process of changing the level of the pressure applied by said pressing device to said pressure sensor, the pressing device including:

a pressure adjusting unit including a gas container of a constant capacity for adjusting the level of the pressure applied to the pressure sensor using pressure of gas in the gas container, and a state changing unit, the gas container including:

an isolation unit keeping a partial amount of an isolated gas, a main unit; and a gas flow adjustment unit configured for adjusting a gas flow passage between the main unit and the isolation unit, wherein the state changing unit is configured for setting the pressure adjusting unit to a gas holding state for holding an amount of the gas in the gas container, changing the gas holding state to a gas isolating and discharging state for isolating and discharging a partial amount of the gas held in the gas container in said gas holding state from the remaining amount of the gas, and changing the gas isolating and discharging state to the gas holding state for holding the remaining amount of the gas in the gas container;

wherein the state changing unit is configured for setting the pressure adjusting unit to a gas supplying state for supplying gas to the gas container; and wherein the pressure adjusting unit further includes a supply source for supplying gas to the gas container in the gas supplying state;

wherein the gas flow adjustment unit is a three-port valve having a main-unit-related port for input/output of gas from/to the main unit, an isolation-unit-related port for input/output of gas from/to the isolation unit and an atmosphere-related port leading to atmosphere; and wherein the state changing unit controls said three-port valve for connecting the isolation-unit-related port to the main-unit-related port in establishing said flow passage, and controls the three-port valve for connecting said isolation-unit-related port to the atmosphere-related port in shutting off the flow passage.

4. The pulse wave measuring apparatus according to claim 3, wherein the isolation unit has a supply-related port for input of gas from the supply source in the gas supplying state, and wherein the state changing unit controls the three-port valve in the gas supplying state for connecting the isolation-unit-related port to the main-unit-related port.

5. The pulse wave measuring apparatus according to claim 4, wherein the state changing unit variably adjusts the period of the gas isolating and discharging state in changing the state from the gas isolating and discharging state to the gas holding state.

* * * * *